US011110196B2

(12) United States Patent
Tee, Jr. et al.

(10) Patent No.: US 11,110,196 B2
(45) Date of Patent: Sep. 7, 2021

(54) ARTICLES COMPRISING MALODOR REDUCTION COMPOSITIONS

(71) Applicant: The Procter & Gamble Company, Cincinnati, OH (US)

(72) Inventors: Johannson Jimmy Tee, Jr., Mason, OH (US); Zaiyou Liu, West Chester, OH (US); Melissa Jane Wene, Lebanon, OH (US); Ann Marie Frey, Cedar Grove, IN (US); Nancy L Schuchter, Cold Spring, KY (US); Gabriele Stiehl, Bad Soden (DE); William Winfield Cheeseman, Mason, OH (US); Judith Ann Hollingshead, Batavia, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1405 days.

(21) Appl. No.: 14/447,662

(22) Filed: Jul. 31, 2014

(65) Prior Publication Data
US 2015/0038928 A1 Feb. 5, 2015

Related U.S. Application Data

(60) Provisional application No. 61/861,062, filed on Aug. 1, 2013.

(51) Int. Cl.
A61L 15/46 (2006.01)
A61F 13/84 (2006.01)

(52) U.S. Cl.
CPC .......... A61L 15/46 (2013.01); A61F 13/8405 (2013.01); A61F 2013/8408 (2013.01)

(58) Field of Classification Search
CPC ......... A61F 13/8405; A61F 2013/8408; A61L 15/46; A61L 9/01; A61L 9/05; A61L 9/012; C08K 2201/007
USPC ........................................................ 604/359
See application file for complete search history.

(56) References Cited

U.S. PATENT DOCUMENTS

| 3,239,478 | A | 3/1966 | Harlan |
| 3,427,269 | A | 2/1969 | Davis et al. |
| 3,700,633 | A | 10/1972 | Wald et al. |
| 3,745,131 | A | 7/1973 | Jaggers et al. |
| 3,753,936 | A | 8/1973 | Marrs |
| 3,932,327 | A | 1/1976 | Naylor |
| 4,359,395 | A | 11/1982 | Schreck et al. |
| 4,515,909 | A | 5/1985 | Sawano et al. |
| 4,582,635 | A | 4/1986 | Furuuchi et al. |
| 5,300,192 | A | 4/1994 | Hansen et al. |
| 5,308,896 | A | 5/1994 | Hansen et al. |
| 5,418,052 | A | 5/1995 | Sugie et al. |
| 5,532,300 | A | 7/1996 | Koubek et al. |
| 5,589,256 | A | 12/1996 | Hansen et al. |
| 5,614,570 | A | 3/1997 | Hansen et al. |
| 5,711,941 | A | 1/1998 | Behan et al. |
| 5,723,222 | A | 3/1998 | Sato et al. |
| 5,849,310 | A | 12/1998 | Trinh et al. |
| 5,951,534 | A | 9/1999 | Cummings et al. |
| 5,981,068 | A | 11/1999 | Tsujiyama et al. |
| 6,086,903 | A | 7/2000 | Trinh et al. |
| 6,120,487 | A | 9/2000 | Buell et al. |
| 6,180,121 | B1 | 1/2001 | Guenin et al. |
| 6,475,473 | B1 | 11/2002 | Perring et al. |
| 6,627,249 | B2 | 9/2003 | Hansen et al. |
| 6,869,923 | B1 | 3/2005 | Cunningham et al. |
| 6,921,581 | B2 | 7/2005 | Van Gelder et al. |
| 7,445,838 | B2 | 11/2008 | Quinn |
| 7,833,515 | B2 | 11/2010 | Corzani et al. |
| 7,884,063 | B2 | 2/2011 | Striepling et al. |
| 8,187,240 | B2 | 5/2012 | Busam et al. |
| 8,319,005 | B2 | 11/2012 | Becker et al. |
| 8,357,359 | B2 | 1/2013 | Woo et al. |
| 8,404,630 | B2 | 3/2013 | Gambogi et al. |
| 8,481,635 | B2* | 7/2013 | Quinn ................. C08L 23/0869 524/515 |
| 9,399,078 | B2* | 7/2016 | Hollingshead ............ A61L 2/16 |
| 2002/0025435 | A1 | 2/2002 | Hansen et al. |
| 2002/0120242 | A1 | 8/2002 | Tyrrell et al. |
| 2002/0132070 | A1 | 9/2002 | Franzen et al. |
| 2003/0105183 | A1 | 6/2003 | Sharak |
| 2003/0206979 | A1 | 11/2003 | Dvoracek et al. |
| 2004/0037792 | A1 | 2/2004 | Hiramoto et al. |
| 2004/0115091 | A1 | 6/2004 | Beerling et al. |
| 2004/0241333 | A1 | 12/2004 | Cielenski et al. |

(Continued)

FOREIGN PATENT DOCUMENTS

| GB | 2 422 780 A | 8/2006 |
| JP | 63189485 | 8/1988 |

(Continued)

OTHER PUBLICATIONS

International Search Report, PCT/US2014/049014, dated Oct. 2, 2014, 10 pages.

Primary Examiner — Andrew J Mensh
(74) Attorney, Agent, or Firm — Daniel S. Albrecht; Kathleen Yates Carter

(57) ABSTRACT

An absorbent article comprising a malodor reduction composition. The malodor reduction composition comprises a perfume mixture comprising about 5% to about 100%, by weight of said perfume mixture, of at least two perfume materials selected from the group consisting of terpinyl acetate, methyl iso-eugenol, phenyl acetaldehyde dimethyl acetal, and patchone.

13 Claims, No Drawings

(56) References Cited

U.S. PATENT DOCUMENTS

| | | |
|---|---|---|
| 2004/0266302 A1* | 12/2004 | DiSalvo .............. A61F 13/8405 442/382 |
| 2005/0032963 A1 | 2/2005 | Harwell et al. |
| 2005/0058674 A1 | 3/2005 | Joseph et al. |
| 2005/0276831 A1 | 12/2005 | Dihora et al. |
| 2006/0165622 A1 | 7/2006 | Hiramoto et al. |
| 2007/0020263 A1 | 1/2007 | Shitara et al. |
| 2007/0020452 A1 | 1/2007 | Hamed et al. |
| 2007/0149639 A1 | 6/2007 | Horikoshi et al. |
| 2007/0185228 A1 | 8/2007 | Dente et al. |
| 2008/0009560 A1 | 1/2008 | McKay, Jr. |
| 2008/0011632 A1 | 1/2008 | Albino |
| 2008/0207476 A1 | 8/2008 | Artiga et al. |
| 2008/0207481 A1 | 8/2008 | Meine et al. |
| 2008/0221003 A1 | 9/2008 | Meine et al. |
| 2008/0305982 A1 | 12/2008 | Smets et al. |
| 2009/0067760 A1 | 3/2009 | Shelley et al. |
| 2009/0081755 A1 | 3/2009 | Schmiedel et al. |
| 2009/0202599 A1 | 8/2009 | Zhou et al. |
| 2009/0257973 A1 | 10/2009 | Fraser et al. |
| 2009/0263344 A1 | 10/2009 | Evans et al. |
| 2009/0269297 A1 | 10/2009 | Conover |
| 2009/0326093 A1 | 12/2009 | Funk et al. |
| 2010/0047198 A1* | 2/2010 | Striepling .......... B01F 17/0085 424/59 |
| 2010/0076389 A1 | 3/2010 | Burrow et al. |
| 2010/0111889 A1 | 5/2010 | Marsh et al. |
| 2010/0115708 A1 | 5/2010 | Caswell et al. |
| 2010/0187135 A1 | 7/2010 | Broering et al. |
| 2010/0247475 A1 | 9/2010 | Mori et al. |
| 2010/0261629 A1 | 10/2010 | Smets et al. |
| 2010/0287710 A1 | 11/2010 | Denutte et al. |
| 2011/0015421 A1 | 1/2011 | Abe et al. |
| 2011/0150814 A1 | 6/2011 | Woo et al. |
| 2011/0150815 A1 | 6/2011 | Woo et al. |
| 2011/0152804 A1 | 6/2011 | Woo et al. |
| 2011/0164834 A1 | 7/2011 | Stiglic et al. |
| 2011/0213120 A1 | 9/2011 | Astrologes et al. |
| 2011/0274634 A1 | 11/2011 | Rieth et al. |
| 2011/0305657 A1 | 12/2011 | Kueper et al. |
| 2012/0316530 A1* | 12/2012 | Armstrong-Ostle ........................ A61F 13/1565 604/366 |
| 2013/0085204 A1* | 4/2013 | Hollingshead ............ A61L 2/16 523/102 |
| 2013/0121950 A1 | 5/2013 | Woo et al. |
| 2013/0266642 A1* | 10/2013 | Hollingshead ............ A61L 9/01 424/451 |
| 2014/0134435 A1 | 5/2014 | Mansfield |
| 2014/0134910 A1 | 5/2014 | Mansfield |

FOREIGN PATENT DOCUMENTS

| | | |
|---|---|---|
| JP | 1988042 | 11/1995 |
| JP | 2001081669 | 3/2001 |
| JP | 2002-272780 | 9/2002 |
| JP | 2004-41407 | 2/2004 |
| JP | 2004-330692 | 11/2004 |
| JP | 2005015686 | 1/2005 |
| JP | 2005-95420 | 4/2005 |
| JP | 2007252886 | 10/2007 |
| JP | 2013/111326 | 6/2013 |
| KR | 2008/0096995 | 11/2008 |
| WO | WO 2000/64500 | 11/2000 |
| WO | WO 02/051456 | 7/2002 |
| WO | WO 2004/098666 | 11/2004 |
| WO | WO 2005/035013 | 4/2005 |
| WO | WO 2005/046632 | 5/2005 |
| WO | WO 2005/120414 | 12/2005 |
| WO | WO 2007/107856 | 9/2007 |
| WO | WO 2008/001240 | 1/2008 |
| WO | WO 2008/068059 | 6/2008 |
| WO | WO 2008104352 A2 * | 9/2008 ......... C11D 3/38627 |
| WO | WO 2008/129028 | 10/2008 |
| WO | WO 2010/149798 | 12/2010 |
| WO | WO 2012/078626 | 6/2012 |
| WO | WO 2012/169576 | 12/2012 |
| WO | WO 2013/18805 | 2/2013 |
| WO | WO 2013/154899 | 10/2013 |

* cited by examiner

ARTICLES COMPRISING MALODOR REDUCTION COMPOSITIONS

FIELD OF THE INVENTION

The present invention relates to absorbent articles comprising unscented and low scented malodor reduction compositions and methods of making and using same.

BACKGROUND OF THE INVENTION

Unscented or low scented products are desired by consumers as they may be considered more natural and discreet than scented products. Manufacturers of unscented or low scented products for controlling malodors rely on malodor reduction ingredients or other technologies (e.g. filters) to reduce malodors. However, effectively controlling both dry and soiled absorbent article malodors may be difficult, and the time required for a product to noticeably reduce malodors may create consumer doubt as to the product's efficacy on malodors. Often times, manufacturers incorporate scented perfumes to help mask these difficult malodors.

U.S. patent application Ser. No. 13/249,616 discloses unscented and low scent malodor reduction compositions that control malodors. Unfortunately, the range of materials used to produce such compositions is more limited than desired. Surprisingly, Applicants recognized that, while perfume raw materials that have high vapor pressures (for example vapor pressures higher than 0.1 torr at 25° C.) are expected to produce significant scent as these materials have a higher number of perfume molecules per unit of air, certain high vapor pressure perfume raw materials produce little or no scent and reduce malodor when used at the level taught herein.

SUMMARY OF THE INVENTION

The present invention relates to absorbent articles comprising unscented and low scented malodor reduction compositions and methods of making and using same.

DETAILED DESCRIPTION OF THE INVENTION

Definitions

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Adhesive" refers to compositions comprising one or more thermoplastic polymers and typically one or more tackifier resins and a rheology modifier or plasticizer. Adhesives may contain 2% or more of a tackifier resin. An adhesive is generally used to join or bond two or more materials together by applying it to at least one material and then bringing it into contact with at least one other material with sufficient force and for a sufficient duration of time, that the adhesive can wet out or spread on each material to join them together (see definition of "tackifier" below).

As used herein "consumer product" means baby care and/or feminine care products or devices intended to be used or consumed in the form in which it is sold, and not intended for subsequent commercial manufacture or modification. Such products include but are not limited to diapers, bibs, wipes; skin care including application of creams, lotions, and other topically applied products for consumer use; tampons and/or feminine napkins.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable" in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

As used herein, "malodor" refers to compounds generally offensive or unpleasant to most people, such as the complex odors associated with bowel movements.

As used herein, "neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Neutralization is distinguishable from odor masking or odor blocking by a change in the malodorous compound, as opposed to a change in the ability to perceive the malodor without any corresponding change in the condition of the malodorous compound. Malodor neutralization provides a sensory and analytically measurable (e.g. gas chromatograph) malodor reduction. Thus, if a malodor reduction composition delivers genuine malodor neutralization, the composition will reduce malodors in the vapor and/or liquid phase.

As used herein, "odor masking" refers to the ability of a compound with a non-offensive or pleasant smell that is dosed such that it limits the ability to sense a malodorous compound. Odor-masking may involve the selection of compounds which coordinate with an anticipated malodor to change the perception of the overall scent provided by the combination of odorous compounds.

"Tackifier" refers to an adhesive component with a glass transition temperature in the range from about 70° C. to about 150° C. that decreases the melt viscosity of a rubbery polymer and increases the rubbery polymer's glass transition temperature and decreases the rubbery polymer's entanglement density.

As used herein, the terms "a" and "an" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Malodor Reduction Compositions

The present invention relates to unscented and low scented malodor reduction compositions and methods thereof. Unscented and low scented malodor reduction compositions of the present invention comprise perfume mixtures that are substantially free of scent. The perceptible perfume scent intensity and malodor efficacy of a composition can be determined using the tests outlined herein.

A malodor reduction composition is provided comprising a perfume mixture comprising an effective amount of methyl palmitate, farnesol, vetivert acetate, undecylenic aldehyde, terpinyl acetate, methyl iso-eugenol, phenyl acetaldehyde dimethyl acetal, patchone and optionally a material selected from the group consisting of benzophenones, diphenyl oxide, melozone, iso nonyl acetate, cedryl methyl ether and mixtures thereof, said malodor reduction composition or said perfume mixture being optionally encapsulated is disclosed. Said malodor reduction composition is identified herein as "Malodor Reduction Composition 1".

In one aspect, said malodor reduction composition's perfume mixture is present in an amount up to 100%, by weight of the malodor reduction composition, alternatively from about 0% to about 100%, alternatively from about 5% to about 100%, alternatively from about 10% to about 100%, alternatively from about 30% to about 100%, alternatively from about 50% to about 100%, alternatively from about 70% to about 100%, alternatively from about 80% to about 100%, alternatively from about 0.001% to about 5%, alternatively from about 0.001% to about 2%, alternatively from about 0.001% to about 0.5%, alternatively from about 0.001% to about 0.3%, alternatively from about 0.001% to about 0.1%, alternatively about 0.001%, by weight of the malodor reduction composition.

In one aspect, said malodor reduction composition comprises cedryl methyl ether, florhydral, helional, vertofix couer, and mixtures thereof.

In one aspect, said malodor reduction composition's perfume mixture comprises at least one aldehyde selected from the group consisting of floral super, 2-ethoxy Benzylaldehyde, 2-isopropyl-5-methyl-2-hexenal, 5-methyl Furfural, 5-methyl-thiophene-carboxaldehyde, p-anisaldehyde, benzylaldehyde, cinnamic aldehyde, decyl aldehyde, Ligustral, Lyral, Melonal, o-anisaldehyde, P.T. Bucinal, thiophene carboxaldehyde, trans-4-decenal, trans trans 2,4-nonadienal, undecyl aldehyde, and mixtures thereof.

In one aspect, said malodor reduction composition's perfume mixture comprises from about 0% to about 100%, from about 5% to about 100%, from about 8% to about 70%, from about 10% to about 50% or even from about 12% to about 30% benzophenone, methyl palmitate, farnesol, vetivert acetate, and undecylenic aldehyde.

In one aspect, said malodor reduction composition's perfume mixture comprises an aldehyde mixture selected from the group consisting of Accord A, Accord B, Accord C, and mixtures thereof. Such accords are given below:

| Accord A | | | |
|---|---|---|---|
| Material | Wt. % (of the aldehydes in the perfume mixture) | CAS Number | VP(torr) @25° C. |
| Intreleven Aldehyde | 5.000 | 112-45-8 | 0.060 |
| Florhydral | 10.000 | 125109-85-5 | 0.008 |
| Floral Super | 25.000 | 71077-31-1 | 0.030 |
| Scentenal | 10.000 | 86803-90-9 | 0.010 |
| Cymal | 25.000 | 103-95-7 | 0.007 |
| o-anisaldehyde | 25.000 | 135-02-4 | 0.032 |

| Accord B | | | |
|---|---|---|---|
| Material | Wt. % (of the aldehydes in the perfume mixture) | CAS Number | VP (torr) @25° C. |
| Intreleven Aldehyde | 2.000 | 112-45-8 | 0.060 |
| Florhydral | 20.000 | 125109-85-5 | 0.008 |
| Floral Super | 10.000 | 71077-31-1 | 0.030 |
| Scentenal | 5.000 | 86803-90-9 | 0.010 |
| Cymal | 25.000 | 103-95-7 | 0.007 |
| Floralozone | 10.000 | 67634-14-4 | 0.005 |
| Adoxal | 1.000 | 141-13-9 | 0.007 |
| Methyl Nonyl Acetaldehyde | 1.000 | 110-41-8 | 0.030 |
| Melonal | 1.000 | 106-72-9 | 0.670 |
| o-anisaldehyde | 25.000 | 135-02-4 | 0.032 |

| Accord C | | | |
|---|---|---|---|
| Material | Wt. % (of the aldehydes in the perfume mixture) | CAS Number | VP (torr) @25° C. |
| Intreleven Aldehyde | 2.000 | 112-45-8 | 0.060 |
| Florhydral | 10.000 | 125109-85-5 | 0.008 |
| Floral Super | 5.000 | 71077-31-1 | 0.030 |
| Scentenal | 2.000 | 86803-90-9 | 0.010 |
| Cymal | 15.000 | 103-95-7 | 0.007 |
| Floralozone | 12.000 | 67634-14-4 | 0.005 |
| Adoxal | 1.000 | 141-13-9 | 0.007 |
| Methyl Nonyl Acetaldehyde | 1.000 | 110-41-8 | 0.030 |
| Melonal | 1.000 | 106-72-9 | 0.670 |
| Flor Acetate | 11.800 | 5413-60-5 | 0.060 |
| Frutene | 7.000 | 17511-60-3 | 0.020 |
| Helional | 5.000 | 1205-17-0 | 0.0005 |
| Bourgeonal | 2.000 | 18127-01-0 | 0.004 |
| Linalool | 10.000 | 78-70-6 | 0.050 |
| Benzaldehyde | 0.200 | 100-52-7 | 1.110 |
| o-anisaldehyde | 15.000 | 135-02-4 | 0.320 |

Accords A, B, or C can be formulated in with the malodor reduction composition's perfume mixture, for example, the perfume mixtures outlined in Tables 1 to 4 of the present specification in an amount of about 5% to about 50%, alternatively about 5% to about 40%, alternatively about 5% to about 30%, alternatively about 5% to about 20%, alternatively about 5% to about 10%, alternatively about 0% to about 5%, by weight of the perfume mixture.

In one aspect, said malodor reduction composition's perfume mixture comprises about 1% to about 10% of Accord A, by weight of said perfume mixture.

In one aspect, said malodor reduction composition comprises, based on total malodor reduction composition weight, from about 0.05% to about 5%, alternatively 0.1% to about 1.5% alternatively about 0.1% to about 1.0%, alternatively about 0.1% to about 0.5%, alternatively about 0.1% to about 0.4%, alternatively about 0.4% to about 1.5%, alternatively about 0.4% of an acid catalyst.

In one aspect, said malodor reduction composition comprises an ingredient selected from the group consisting of: odor masking agents, odor blocking agents, diluents, and mixtures thereof.

A malodor reduction composition comprising a perfume mixture comprising *Styrax* coeur and an effective amount of at least one perfume material selected from the group consisting of: terpinyl acetate, methyl iso-eugenol, phenyl acetaldehyde dimethyl acetal, patchone, and mixtures thereof said malodor reduction composition or said perfume mixture being optionally encapsulated is disclosed. Said malodor reduction composition is identified as "Malodor Reduction Composition 2".

A malodor reduction composition comprising a perfume mixture comprising from about 5% to about 100%, from about 5% to about 25%, from about 8% to about 70%, from about 10% to about 50% or even from about 12% to about 30% by weight of said perfume mixture, of at least two, at least three or at least four perfume materials selected from the group consisting of terpinyl acetate, methyl Iso-eugenol, phenyl acetaldehyde dimethyl acetal, and patchone, said malodor reduction composition or said perfume mixture being optionally encapsulated is disclosed. Said malodor reduction composition is identified as "Malodor Reduction Composition 3".

A malodor reduction comprising a perfume mixture comprising an effective amount or from about 5% to about 100%, from about 5% to about 25%, from about 8% to about 70%, from about 10% to about 50% or even from about 12% to about 30% by weight of said perfume mixture, of at least three perfume materials selected from the group consisting of methyl palmitate, farnesol, vetivert acetate, undecylenic aldehyde, terpinyl acetate, methyl iso-eugenol, phenyl acetaldehyde dimethyl acetal, and patchone, said malodor reduction composition or said perfume mixture being optionally encapsulated is disclosed. Said malodor reduction composition is identified as "Malodor Reduction Composition 4".

In one aspect, said malodor reduction composition's perfume mixture comprises cedryl methyl ether, florhydral, helional, undecylenic aldehyde, vetivert acetate, vertofix couer, and mixtures thereof Additional Perfume Materials Additional perfume materials that may be used include Benzophenone, Methyl Palmitate, Farnesol, Vetivert Acetate, Cedryl Methyl Ether, Vertofix Couer (methyl cedrylone), and mixtures thereof. Suitable perfume materials may also include Helional (alpha-methyl-3,4-(methylenedioxy)-hydrocinnamaldehyde), Florhydral, Undecylenic Aldehyde, Adoxal (2,6,10-Trimethyl-9-undecenal), Bourgeonal (4-t-butylbenzenepropionaldehyde), Cymal, Florhydral (3-(3-isopropyl-phenyl)-butyraldehyde), Citronellal (3,7-dimethyl 6-octenal), Floralozone (para-ethyl-alpha,alpha-dimethyl hydrocinnamaldehyde), Floral Super, Pino Acetaldehyde, *Styrax* Coeur.

Suitable perfume materials may also include volatile aldehydes or reactive aldehydes (RA) including, but not limited to, Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylproionaldehyde, 4-dimethylbenzenepropanal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Tricyclo5210-2,6decylidene-8butanal), Melafleur (1,2,3,4,5,6,7,8-octahydro-8,8-dimethyl-2-naphthaldehyde), Methyl Octyl Acetaldehyde, aldehyde C-11 MOA (2-methyl deca-1-al), Onicidal (2,6,10-trimethyl-5,9-undecadien-1-al), Muguet aldehyde 50 (3,7-dimethyl-6-octenyl)oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylproprionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1-cyclohexene-1-carboxaldehyde).

Suitable aldehydes may also include acetaldehyde (ethanal), pentanal, valeraldehyde, amylaldehyde, Scentenal (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl 2-butenal), 2-Methyl-3-(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenylpropenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexyl-cinnamaldehyde), Acalea (p-methyl-alpha-pentylcinnamaldehyde), methylcinnamaldehyde, alpha- Methylcinnamaldehyde (2-methyl 3-pheny propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4(1-methylethenyl)-1-cyclohexene-1-carboxaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax, Corps Iris, Maceal, and Corps 4322.

Table 1 shows one embodiment of a perfume mixture suitable for the malodor reduction composition of the present invention.

TABLE 1

Low Scent Mixture Composition A

| Material name | Weight % | CAS # |
|---|---|---|
| Diphenyl oxide | 0.5 | 101-84-8 |
| Melozone | 0.5 | 30772-79-3 |
| Undecylenic Aldehyde | 1 | 112-45-8 |
| Benzophenone | 5 | 119-61-9 |
| Iso nonyl acetate | 5 | 58430-94-7 |
| Undecyl aldehyde | 5 | 112-45-8 |
| Cedryl Methyl ether | 10 | 19870-74-7 |
| Methyl iso eugenol | 23 | 93-16-3 |
| Phenyl acetaldehyde dimethyl acetal | 25 | 101-48-4 |
| Terpinyl acetate | 25 | 80-26-2 |
| TOTAL | 100.00 | |

Tables 2 & 3 show other embodiments of a perfume mixture suitable for the malodor reduction compositions of the present invention.

TABLE 2

Low Scented Mixture Composition B

| Material name | Weight % | CAS # |
|---|---|---|
| 5-Cyclohexadecen-1-One | 4 | 37609-25-9 |
| Cedryl Methyl Ether | 0.5 | 19870-74-7 |
| Florhydral | 1 | 125109-85-5 |
| Helional | 0 | 1205-17-0 |
| Vertofix Coeur | 20 | 32388-55-9 |
| Undecylenic Aldehyde | 0.2 | 112-45-8 |
| Methyl palmitate | 15 | 112-39-0 |
| Vetivert Acetate | 0.5 | 68917-34-0 |
| Farnesol | 15 | 4602-84-0 |
| Adoxal | 0.8 | 141-13-9 |
| Methyl Iso Eugenol | 10 | 93-16-3 |
| Terpinyl Acetate | 10 | 80-26-2 |
| Phenyl Acetaldehyde Dimethyl Acetal | 10 | 101-48-4 |
| Patchon | 13 | 98-52-2 |
| TOTAL | 100.00 | |

TABLE 3

Low Scented Mixture Composition C

| Material Name | Weight % | CAS # |
|---|---|---|
| Cedryl Methyl Ether | 0.50 | 19870-74-7 |
| Florhydral | 1.00 | 125109-85-5 |
| Helional | 0.00 | 1205-17-0 |
| Vertofix Coeur | 20.00 | 32388-55-9 |
| Undecylenic Aldehyde | 0.20 | 112-45-8 |
| Methyl palmitate | 15.00 | 112-39-0 |
| Vetivert Acetate | 1.00 | 68917-34-0 |
| Farnesol | 15.00 | 4602-84-0 |
| Adoxal | 0.80 | 141-13-9 |
| Methyl Iso Eugenol | 16.50 | 93-16-3 |
| Terpinyl Acetate | 20.00 | 80-26-2 |
| Phenyl Acetaldehyde Dimethyl Acetal | 10.00 | 101-48-4 |
| TOTAL | 100.00 | |

Table 4 shows yet another embodiment of a perfume mixture suitable for the malodor reduction composition of the present invention.

TABLE 4

Plastic Low Scented Mixture Compositions D and E

| Material Name | Composition D Weight % | Composition E Weight % | CAS # |
|---|---|---|---|
| 5-Cyclohexadecen-1-One | 4.00 | 4.00 | 37609-25-9 |
| Cedryl Methyl Ether | 0.50 | 0.50 | 19870-74-7 |
| Florhydral | 1.00 | 1.00 | 125109-85-5 |
| Helional | 0.00 | 0.00 | 1205-17-0 |
| Vertofix Coeur | 14.50 | 20.00 | 32388-55-9 |
| Undecylenic Aldehyde | 0.20 | 0.20 | 112-45-8 |
| Methyl palmitate | 16.00 | 15.00 | 112-39-0 |
| Vetivert Acetate | 0.50 | 0.50 | 68917-34-0 |
| Farnesol | 15.00 | 15.00 | 4602-84-0 |
| Adoxal | 0.80 | 0.80 | 141-13-9 |
| Methyl Iso Eugenol | 10.00 | 10.00 | 93-16-3 |
| Terpinyl Acetate | 10.00 | 10.00 | 80-26-2 |
| Phenyl Acetaldehyde Dimethyl Acetal | 10.00 | 10.00 | 101-48-4 |
| Patchon | 13.00 | 13.00 | 98-52-2 |
| Styrax Coeur | 4.5 | 0 | 8046-19-3 |
| TOTAL | 100.00 | 100.00 | |

In some embodiments, the malodor reduction composition includes a mixture of perfume materials identified in Tables 1-4 along with a mixture of two or more aldehydes selected from the group consisting of 2-ethoxy Benzylaldehyde, 2-isopropyl-5-methyl-2-hexenal, 5-methyl Furfural, 5-methyl-thiophene-carboxaldehyde, p-anisaldehyde, Benzylaldehyde, Cinnamic aldehyde, Decyl aldehyde, Ligustral, Lyral, Melonal, o-anisaldehyde, P.T. Bucinal, Thiophene carboxaldehyde (TC), trans-4-Decenal, trans trans 2,4-Nonadienal, Undecyl aldehyde, and mixtures thereof. In some embodiments where volatility is not important for neutralizing a malodor, the present invention may include poly-aldehydes, for example, di-, tri-, tetra-aldehydes.

Process of Making Encapsulates

Methods of making suitable encapsulated malodor reduction compositions, for example condensation processes, as well as suitable shell materials for such encapsulated malodor reduction compositions are described in U.S. Pat. No. 6,869,923 B1 and US Published Patent Applications Nos. 2005/0276831 A1 and 2007/020263 A1. Such shell materials include acrylates, acrylics, aminoplast materials such as melamine formaldehyde material and combinations thereof. Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Optional Ingredients

The malodor reduction composition may, optionally, include odor masking agents and/or diluents.

Water and surfactants may also be present in any amount for the composition to make an aqueous solution. In some embodiments, water may be present in an amount of about 85% to 99.5%, alternatively about 90% to about 99.5%, alternatively about 92% to about 99.5%, alternatively about 95%, by weight of said malodor reduction composition. Water containing a small amount of low molecular weight monohydric alcohols, e.g., ethanol, methanol, and isopropanol, or polyols, such as ethylene glycol and propylene glycol, can also be useful.

The malodor reduction composition may also comprise 100% of an unscented or low scented perfume mixture according to the present invention.

The malodor reduction composition of the present invention may be combined with one or more diluents. When combined with said diluents, the malodor reduction composition may comprise from about 1 to about 80% or from about 5% to about 50% or from about 10% to about 30% of the total mixture. For use in the present invention, diluents with low scent intensity are preferred, but not required. Exemplary diluents include DBE-LVP (Mixed aliphatic ester fluid (CAS #1119-40-0 and CAS #627-93-0 from INVISTA), dipropylene glycol methyl ether, 3-methoxy-3-methyl-1-butanol, isononyl acetate, benzyl alcohol, florol, dioctyl adipate (CAS #123-79-5), Tripropylene glycol Methyl ether (CAS #25498-49-1), Dow Corning 200® Fluid, 1.5 CST®. (from the Dow Corning Co.), Dipropylene glycol n-propyl ether, Xiameter® PMX-200 Silicone Fluid 1.5CS® (from the Dow Corning Co.), cellulose, Ethyl ether and mixtures thereof. Additional diluents may include DPG (dipropylene glycol), iso propyl myristate, tri ethyl citrate, or mixtures thereof.

Articles of Manufacture Comprising Malodor Reduction Compositions and Methods of Using Such Compositions The malodor reduction composition of the present invention may be used in a wide variety of applications that neutralize malodors in the vapor and/or liquid phase.

Absorbent Articles

In general, the absorbent articles of the present invention typically comprise a topsheet, a backsheet, and an absorbent core disposed between the topsheet and backsheet.

The topsheet of the absorbent article is preferably compliant, soft feeling, and non-irritating to the wearer's skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise multiple layers, such as a woven or nonwoven material, polymeric films such as thermoplastic films of polyethylene or polypropylene, or composite materials such as a film-coated nonwoven material.

The backsheet and the topsheet can be positioned adjacent the garment surface and the body surface, respectively, of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa. The absorbent core can comprise superabsorbent materials such as absorbent gelling materials (AGM), including AGM fibers, as is known in the art.

The core assembly may include one or more layers of liquid absorbing material. In certain embodiments, the absorbent core assembly may include multiple layers, where each layer is intended to serve a particular purpose. For example, one or more layers may be fluid handling layers (e.g., acquisition layers and/or distribution layers which are not intended to permanently store liquid), while one or more other layers are configured to be storage layers for the permanent storage of liquid. The absorbent core assembly may also include layers to stabilize other core components such as, for example, a core cover and/or dusting layer.

The absorbent article can comprise other additional components, for example between the topsheet and absorbent core, such as a secondary topsheet or acquisition layer (AQL). The secondary topsheet or acquisition layer can comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent article can comprise further components such as side or leg cuffs, typically found in diapers, or side wings or side flaps, typically found in sanitary napkins. The article may comprise side panels attached to the backsheet. The article may be permanently sealed at the sides to configure pants. Or the side panels may include means to releasably attach the side panels to another part of the article to create a pants configuration that can be opened and refastened. Exemplary outer surface fasteners include mechanical fasteners such as a plurality of hooks engaging with loops formed by fibers in a nonwoven sheet.

The absorbent articles herein are preferably disposable after a single use.

The malodor reduction composition of the present invention can be disposed in various locations in the absorbent article. The malodor reduction composition can be disposed on the garment-facing side or the body-facing side of the topsheet or absorbent core, or the body-facing side of the backsheet. The malodor reduction composition may be disposed on the absorbent core, such as on the garment-facing side of the absorbent core. The malodor reduction composition can also be disposed on other components, when present in the absorbent article, such as the garment-facing side of a nonwoven dusting layer or body-facing side of a secondary topsheet or acquisition layer. In some embodiments, a topsheet or an acquisition layer may comprise a tissue layer and/or a nonwoven layer, and the malodor reduction composition may be disposed on either the tissue layer or the nonwoven layer.

As discussed below, the malodor reduction composition may be in the absorbent article via incorporation into an adhesive. In some embodiments, the malodor reduction composition may be incorporated into the absorbent article via a lotion that is applied to a substrate component of the article. In some embodiments, the malodor reduction composition may be incorporated into the absorbent article via an elastomeric film. In some embodiments, the malodor reduction composition may be in an article by having been incorporated into the making of an article component, including, but not limited to, a film, a nonwoven, AGM, elastics, and/or ink.

Adhesives

The absorbent articles disclosed herein may further comprise one or more adhesives. The adhesive may be a construction or chassis adhesive, or any of a number of other types of adhesives that are typically used in absorbent articles. Commonly used adhesives include hot-melt adhesives (i.e., adhesives that exhibit fluid or fluid-like behavior when exposed to a particular temperature or range of temperatures), and may be used to join nonwoven and/or films to each other and/or other absorbent article components. Traditional hot-melt adhesives are well-known in the art and generally have a formulation that includes a polymer for providing cohesive strength, a tackifying resin or analogous material for providing adhesive strength, waxes, plasticizers, or other materials for modifying viscosity (i.e., flowability), and/or other additives including, but not limited to, antioxidants or other stabilizers, pigments, and/or fillers.

In some embodiments, the hot-melt adhesive may comprise a malodor reduction composition. That is, in some embodiments, the hot melt adhesive may serve as the carrier to incorporate the malodor reduction composition into the absorbent article. The malodor reduction composition may be added to hot melt adhesives with or without encapsulation or other protective means. The malodor reduction compositions are capable of remaining stable in the adhesives prior to their use in absorbent articles and while used in absorbent articles. The malodor reduction compositions are used in the process at a suitable level to achieve the desired effect in terms of reducing malodor of the article. The effective amount of malodor reduction composition may be from about 0.020% to about 0.75%, by weight of the adhesive, or in some cases from about 0.04%, 0.06%, 0.08%, 0.1%, 0.2%, 0.3%, 0.4%, 0.5%, 0.6%, or 0.7% to about 0.75%, 0.7%, 0.6%, 0.5%, 0.4%, 0.3%, 0.2%, 0.1%, 0.08%, 0.06%, 0.04%, or 0.03%, with every combination therein.

Conventional hot-melt adhesives are typically liquefied, for example, using a hot-melt tank and subsequently transported via a pump to the point of application (e.g., the surface of a substrate). The adhesive, which may include the malodor reduction composition, is typically applied to a substrate while the adhesive is in a molten state and then contacted with a different substrate or another portion of the same substrate to form a laminate structure. The adhesive can be applied to one or more portions of one or more substrates such as a nonwoven or film web by any suitable method known in the art (e.g., coating or spraying) in an amount sufficient to enable a suitable adhesive bond to be formed between the substrates. The substrate may be a nonwoven, film, tissue, scrim, mesh, combinations of these and the like, such as the materials disclosed above for use in absorbent articles. The attachment may be formed by any of a variety of attachment methods or mechanisms. For example, the attachment methods or mechanisms may include a uniform continuous layer of adhesive, a patterned layer of adhesive, or an array of separate lines, spirals, or spots of adhesive.

An adhesive comprising a malodor reduction composition may be applied and incorporated into an absorbent article in numerous ways. For example, the adhesive comprising a malodor reduction composition may be used to adhere a backsheet nonwoven to a backsheet film, a topsheet to the absorbent core, or a topsheet to an acquisition layer. The adhesive may be used to bond an acquisition layer to a nonwoven and/or a film. It may be used to adhere any of the fastener parts to the outer surface or side panels of the article. It may be applied in the vicinity of the leg cuffs as a sealant. The adhesive may be any type of adhesive that is being used between the topsheet and backsheet of a diaper, adult- and/or feminine care product, or even inside a hygiene product. The adhesives of the present invention may be used within or near the core to immobilize the core, immobilize absorbent material, or to bond the core substrate to the core absorbent polymer material, among other uses. The construction of the absorbent core and adhesives used within the core may be such as described in U.S. Pat. Nos. 8,319,005 and 8,187,240, and in U.S. Publication No. 2012/0316530. In some embodiments, the adhesive may be fibrous or be a net-like structure. The adhesive may be used to bond any elastomeric entity to a nonwoven or to a film.

Any adhesive contributing either to the overall product integrity and/or functionality, i.e. lamination of layers, product sealings, AGM immobilization, or fluid handling (hydrophilic adhesives) may be an adhesive comprising the malodor reduction composition.

In certain embodiments, an absorbent article may include one or more end-flap seal, end seals, and/or side seals. In certain embodiments, an end-flap seal may be formed by joining the topsheet to the backsheet along one or both longitudinal ends of the article with an adhesive. Suitable amounts of adhesive for forming an end-flap seal include amounts of between 2.5 and 5.0 grams of adhesive per square meter of substrate.

The adhesive incorporating the malodor reduction composition may be, for example, adhesives sold under the trade names HL1358LO and D3166 ex, by H.B. Fuller Co., St. Paul, Minn. Another suitable adhesive is sold under the trade name DM526 by Henkel of Bridgewater, N.J. Still another example of a suitable adhesive is sold under the trade name 2898 by Bostik, Inc., Wauwatosa, Wis.

Suitable base polymers for use in formulating hot-melt adhesives as disclosed herein include, without limitation, block or multi-block copolymers having the general configuration: A-B-A or A-B-A-B-A-B. The polymer blocks A may be non-rubbery polymer blocks, which have glass transition temperatures above 20° C. (as homopolymers). Suitable examples for polymer blocks A include, without limitation, homopolymers or copolymers of vinyl monomers such as vinyl arenes, vinyl pyridines, vinyl halides and vinyl carboxylates; homopolymers or copolymers of acrylic monomers such as acrylonitrile, methacrylonitrile, and esters of acrylic acids; monovinyl aromatic hydrocarbons of the benzene series such as styrene, vinyl toluene, vinyl xylene, ethyl vinyl benzene; dicyclic monovinyl compounds such as vinyl naphthalene and the like; polymer blocks derived from alpha olefins, alkylene oxides, acetals, and urethanes. The rubbery polymer blocks B may include butadiene, isoprene, propylene, butylene, and/or ethylene, which is partially or substantially hydrogenated. Common examples of rubbery block copolymers include, without limitation, polystyrene-polybutadiene-polystyrene ("SBS"), polystyrene-polyisoprene-polystyrene ("SIS") and polystyrene-poly-(ethylenebutylene)-polystyrene ("SEBS") and polystyrene-poly-(ethylenepropylene)-polystyrene ("SEPS"). These copolymers may be prepared using methods taught, for example, in U.S. Pat. Nos. 3,239,478; 3,427,269; 3,700,633; 3,753,936; and 3,932,327. Suitable rubbery block copolymers may also be obtained from Shell Chemical Co. under the trademarks KRATON 1101, 1102, 1107, 1650, 1652 and 1657; from Enichem under the tradename EUROPRENE; and from Firestone Tire and Rubber Company under the tradename STEREON 840A. Mixtures of copolymers such as blends of SBS and SIS may also be used. The block copolymer component of the adhesive will generally be present at a level of from 10 to 25% by weight of the adhesive composition.

The hot melt adhesives used in the present invention may be polyolefin-based adhesives. Exemplary polyolefin-based adhesives may include those disclosed in U.S. Ser. Nos. 13/673,277 and 13/673,304, respectively. Such adhesives may include at least one homogeneous ethylene/α-olefin interpolymer which is an interpolymer of ethylene and at least one C3-C20 α-olefin.

Hot-melt adhesives for use herein may also include one or more waxes. Suitable waxes include petroleum derived wax and conventional wax. The term "petroleum derived wax" includes both paraffin and microcrystalline waxes having melting points of from 130° F. to 225° F. and synthetic waxes such as low molecular weight polyethylene or Fisher-Tropsch waxes. Commercially available examples of suitable microcrystalline waxes include, without limitation, MICROSERE 5999 (melting point of 90.5° C.) and MICROSERE 5812 (melting point of 85° C.) both available from IGI. Amounts of microcrystalline wax present in a hot-melt adhesive may range from 1 to 10 wt % by weight of the adhesive composition.

Tackifying resins useful in the disclosed hot-melt adhesive compositions include hydrocarbon resins, synthetic polyterpenes, rosin esters, natural terpenes, and the like. The tackifying agent may be present at a level of from 40 to 70% by weight of the adhesive composition, e.g., 60% by weight. More particularly, and depending upon the particular base polymer, the useful tackifying resins may include any compatible resins or mixtures thereof such as natural and modified rosins including, for example, as gum rosin, wood rosin, tall oil rosin, distilled rosin, hydrogenated rosin, dimerized rosin, and polymerized rosin; glycerol and pentaerythritol esters of natural and modified rosins, including, for example as the glycerol ester of pale wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natural terpenes, including, for example, styrene/terpene and alpha methyl styrene/terpene; polyterpene resins having a Ring and Ball softening point, as determined by ASTM method E28-58T, of from about 80° C. to 150° C.; phenolic modified terpene resins and hydrogenated derivatives thereof including, for example, the resin product resulting from the condensation, in an acidic medium, of a bicyclic terpene and a phenol; aliphatic petroleum hydrocarbon resins having a Ball and Ring softening point of from about 70° C. to 135° C.; aromatic petroleum hydrocarbon resins and the hydrogenated derivatives thereof; and alicyclic petroleum hydrocarbon resins and the hydrogenated derivatives thereof. Mixtures of two or more of the above described tackifying resins may be used for some formulations. Also included are the cyclic or acyclic $C_5$ resins and aromatic modified acyclic or cyclic resins. It may be particularly desirable to use one or more natural rosin esters as the tackifier, due to their sustainability (i.e., replenished by nature).

One or more plasticizing or extending oils may be present in the hot-melt adhesive in amounts of from 15% to 30% (e.g., 21%, by weight of the adhesive). Suitable examples of plasticizing or extending oils include olefin oligomers and low molecular weight polymers, vegetable and animal oil, and their derivatives. The petroleum derived oils may be relatively high boiling materials containing only a minor proportion of aromatic hydrocarbons (e.g., less than 30% or even less than 15% by weight of the oil). It may be desirable to use oil that is entirely non-aromatic. Suitable oligomers include polypropylenes, polybutenes, hydrogenated polyisoprene, hydrogenated polybutadiene, or the like having average molecular weights between 350 and 10,000. Examples of oils suitable for use herein include LUMINOL T350, a mineral oil available from Petrocanada and KAYDOL OIL available from Witco Corporation. Naphthenic oils, such as Calsol 5550, available from Calumet may also be useful.

Additives such as antioxidants, stabilizers, and/or pigments may also be included in the disclosed hot-melt adhesive in amounts of up to 3% by weight (e.g., 0.5% by weight). Nonlimiting examples of additives include hindered phenols or hindered phenols in combination with a secondary antioxidant such as distearyl thiodipropionate ("DSTDP") or dilauryl thio-dipropionate ("DLTDP"). Representative examples of hindered phenols include: 1,3,5- trimethyl 2,4,6-tris(3,5-di-tert-butyl-4-hydroxybenzyl)benzene; pentaerythrityl tetrakis-3 (3,5-di-tert-butyl-4-hydroxyphenyl)propionate; pentaerythritol tetrakis(3-lauryl thiodipropionate); n-octadecyl-3,5-di-tert-butyl-4-hydroxyphenol)-propionate; 4,4'-methylenebis(2,6-tert-butylphenol); 4,4'-thiobis(6-tert-butyl-o-cresol); 2,6-di-tertbutylphenol; 6-(4-hydroxyphenoxy)-2,4-bis(n-octyl-thio)-1,3,5-triazine; di-n-octadecyl 3,5-di-tert-butyl-4-hydroxy-benzylphosphonate; 2-(n-octylthio)ethyl 3,5-di-tert-butyl-4-hydroxy-benzoate; and sorbitol hexa[3-(3,5-di-tert-butyl-4-hydroxyphenyl)-propionate]. Commercial examples include IRGAFOS 168, a secondary antioxidant available from Ciba and IRGANOX 1010, a hindered phenol primary antioxidant available from Ciba-Geigy. Other antioxidants include ETHANOX 330, a hindered phenol from Albermarle; SANTOVAR, a 2,5 ditert-amyl hydroquinone from Monsanto; and NAVAGARD P a tris(p-nonylphenyl)phosphite from Uniroyal. Other additives conventionally used in hot-melt adhesives to satisfy different properties and meet specific application requirements also may be included. Such additives include, for example, fillers, pigments, flow modifiers, dyestuffs, which may be incorporated in minor or larger amounts into the adhesive formulation, depending on the purpose.

EXAMPLES

Example 1

Freshening Composition for Absorbent Articles

|  | Example 1-A | Example 1-B | Example 1-C |
|---|---|---|---|
| Perfume* | 0 | 0-5 | 10-20 |
| Malodor Reduction Composition B of Table 2 | 5-25 | 10-30 | 10-20 |
| Diluent A as given below | 75-95 | Balance | Balance |

*Any desired perfume can be used.

Ranges are Weight % Based on Total Composition

Diluent A may be 100% iso propyl myristate, a combination of iso propyl myristate and dipropylene glycol in a ratio of 1:3 to 3:1, or a combination of iso propyl myristate and dipropylene glycol in any ratio from 1:2 to 1:4 or 2:1 to 4:1. Diluent A can also be 100% dipropylene glycol. Another diluent could be TEC (Tri ethyl citrate).

The composition of Example 1 may be disposed on a substrate that is incorporated into an absorbent article, such as a nonwoven dusting layer, backsheet, topsheet, absorbent core, or acquisition layer, or the composition may be mixed into a hot melt tank with other hot melt adhesive components, and then incorporated into an absorbent article.

Example 2

Freshening Composition for Absorbent Articles

|  | Example 2-A | Example 2-B | Example 2-C |
|---|---|---|---|
| Perfume* | 0 | 0-5 | 10-20 |
| Malodor Reduction Composition E of Table 4 | 5-25 | 10-30 | 10-20 |
| Diluent A as given above | 75-95 | Balance | Balance |

*Any desired perfume can be used

The composition of Example 2 may be disposed on a substrate that is incorporated into an absorbent article, such as a nonwoven dusting layer, backsheet, topsheet, absorbent core, or acquisition layer, or the composition may be mixed into a hot melt tank with other hot melt adhesive components, and then incorporated into an absorbent article.

Sensory Test—Effect of Malodor Reduction Compositions on Dry Diapers

Malodor reduction compositions H1957-1 and H1957-3 (Tables 5 and 6, respectively) are evaluated on dry diapers.

TABLE 5

| Raw Material Name | Wet % | CAS Number |
|---|---|---|
| Perfume Formula H1957-1 | 100.00% |  |
| Dihydro Cyclacet | 15.00% |  |
| Plicatone | 6.00% | 41724-19-0 |
| Vetivert Acetate | 2.00% | 68917-34-0 |
| Flor Acetate | 15.00% | 54830-99-8 |
| Frutene | 8.00% | 68912-13-0 |
| Cedryl Methyl Ether | 10.00% | 19870-74-7 |
| Methyl palmitate | 5.00% | 112-39-0 |
| Farnesol | 5.00% | 4602-84-0 |
| Undecyl Aldehyde | 2.00% | 112-45-8 |
| Undecylenic Aldehyde | 1.00% | 112-45-8 |
| Melozone | 0.50% |  |
| Vertofix Coeur | 1.00% | 32388-55-9 |
| Diphenyl Oxide | 0.50% | 101-84-8 |
| Terpinyl Acetate | 10.00% | 80-26-2 |
| Phenyl Acetaldehyde Dimethyl Acetal | 4.00% | 101-48-4 |
| Methyl Iso Eugenol | 15.00% | 93-16-3 |
| TOTALS: | 100.00% |  |

TABLE 6

| Perfume Formula H1957-3 | CAS Number | Wet Wt % |
|---|---|---|
| Diphenyl Oxide | 101-84-8 | 0.50 |
| Melozone | 30772-79-3 | 0.50 |
| Undecylenic Aldehyde | 112-45-8 | 1.00 |
| Iso Nonyl Acetate | 58430-94-7 | 5.00 |
| Undecyl Aldehyde | 112-45-8 | 5.00 |
| Cedryl Methyl Ether | 19870-74-7 | 10.00 |
| Methyl Iso Eugenol | 93-16-3 | 23.00 |
| Phenyl Acetaldehyde Dimethyl Acetal | 101-48-4 | 25.00 |
| Terpinyl Acetate | 80-26-2 | 28.00 |
| Vertofix Coeur | 32388-55-9 | 2.00 |
| TOTALS: |  | 100.00 |

The method is as follows:

The malodor reduction composition is hand-injected on the core of a diaper. Each sample is a single diaper. The control is an unscented Pampers diaper. Each sample for headspace analysis is placed in a 2 liter jar and allowed to equilibrate for approximately 16 hours before evaluation.

An evaluation is done by three graders, each of whom has extensive experience in odor/perfume evaluations. One sample is prepared for each grader. Each grader opens the jar and sniffs the headspace. Once each grader has sniffed the jar, the three graders discuss the odor character and assign an odor intensity rating on a 0-100 point scale. The final grade is a consensus grade for all three graders. If they cannot agree on a single value, value ranges are permitted, or an average may be assigned. A grade of at least 10 is considered a meaningful difference in odors by the graders.

Scale: All evaluations are made on a 0-100 point intensity scale.
  Malodor: 0=no odor; 50=moderate odor; 100=extremely high odor.
  Perfume: 0=no perfume; 50=moderate perfume intensity; 100=extremely high perfume intensity.

The graders also record odor character comments as part of the assessment. The odor character is described in words that are consumer-like terms, rather than chemical terms.

Table 7 summarizes the results of the odor intensity and character for two different malodor reduction compositions, each at two levels. The compositions were added to the same type of diaper as the control. The malodor reduction compositions of the present invention show meaningful malodor reduction at 3 uL/diaper.

TABLE 7

Sensory Test Results

| Test Products | Odor Grade | Comments |
|---|---|---|
| Control | 60-65 | Glue, Solvent |
| H1957-1 @ 1 uL | 50-55 | Solvent |
| H1957-1 @ 3 uL | 30 | Less strong perfume, less solvent |
| H1957-3 @ 1 uL | 50 | Solvent |
| H1957-3 @ 3 uL | 25-30 | Powdery, slightly more perfumery, less solvent |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. An absorbent article comprising a topsheet, a backsheet, an absorbent core disposed between the topsheet and the backsheet, and a hot melt adhesive comprising a homogeneous linear ethylene/C3-C20 α-olefin interpolymer, wherein a portion of the hot melt adhesive is disposed within the absorbent core, wherein the hot melt adhesive comprises a malodor reduction composition comprising a perfume mixture, wherein the hot melt adhesive comprises from about 0.020% to about 0.75%, by weight of the hot melt adhesive, of the malodor reduction composition, wherein the perfume mixture comprises at least two perfume materials selected from the group consisting of terpinyl acetate, methyl iso-eugenol, phenyl acetaldehyde dimethyl acetal, and patchone, and wherein the perfume mixture comprises from about 5% to about 30%, by weight of the perfume mixture, of the terpinyl acetate and the methyl iso-eugenol.

2. The absorbent article of claim 1, wherein the malodor reduction composition comprises cedryl methyl ether, undecylenic aldehyde, methyl palmitate, and mixtures thereof.

3. The absorbent article of claim 1, wherein the malodor reduction composition comprises a diluent.

4. The absorbent article of claim 1, wherein the hot melt adhesive adheres the backsheet to the topsheet.

5. The absorbent article of claim 1, wherein the backsheet comprises a nonwoven layer and a film layer, and wherein the hot melt adhesive adheres the backsheet nonwoven layer to the backsheet film layer.

6. The absorbent article of claim 1, wherein the article comprises an acquisition layer that is disposed between the topsheet and the absorbent core, and wherein the hot melt adhesive adheres the acquisition layer to the topsheet.

7. The absorbent article of claim 1, wherein the absorbent article comprises about 3 uL of the malodor reduction composition.

8. The absorbent article of claim 1, wherein the absorbent core comprises a core substrate and an absorbent polymer material, and wherein the hot melt adhesive joins at least a portion of the absorbent polymer material to the core substrate.

9. An absorbent article comprising a topsheet, a backsheet, an absorbent core disposed between the topsheet and the backsheet, an acquisition layer disposed between the topsheet and the absorbent core, and a hot melt adhesive comprising a first homogeneous linear ethylene/α-olefin interpolymer and a second homogeneous ethylene α-olefin interpolymer, wherein the hot melt adhesive is free of tackifier, wherein a portion of the hot melt adhesive is disposed within the absorbent core, wherein the hot melt adhesive comprises a malodor reduction composition, wherein the hot melt adhesive comprises from about 0.020% to about 0.75% by weight of the malodor reduction composition, wherein the malodor reduction composition comprises at least three perfume materials selected from the group consisting of methyl palmitate, farnesol, vetivert acetate, undecylenic aldehyde, terpinyl acetate, methyl iso-eugenol, phenyl acetaldehyde dimethyl acetal, and patchone, and wherein the perfume mixture comprises from about 5% to about 30%, by weight of the perfume mixture, of the terpinyl acetate and the methyl iso-eugenol.

10. The absorbent article of claim 9, wherein the hot melt adhesive adheres the backsheet to the topsheet.

11. The absorbent article of claim 9, wherein the backsheet comprises a nonwoven layer and a film layer, and wherein the hot melt adhesive adheres the backsheet nonwoven layer to the backsheet film layer.

12. The absorbent article of claim 9, wherein the absorbent article comprises about 3 uL of the malodor reduction composition.

13. The absorbent article of claim 9, wherein the absorbent core comprises a core substrate and an absorbent polymer material, and wherein the hot melt adhesive joins at least a portion of the absorbent polymer material to the core substrate.

\* \* \* \* \*